(12) United States Patent
Levit et al.

(10) Patent No.: US 12,320,547 B2
(45) Date of Patent: Jun. 3, 2025

(54) AIR SANITIZER WITH BOUNDLESSLY-EXTENDED SANITIZING CHAMBER AND METHOD OF USING SAME

(71) Applicant: DDD Technology Corp., Brooklyn, NY (US)

(72) Inventors: Eyal Konstantine Levit, Brooklyn, NY (US); Oleg Osadchuk, Moscow (RU); Eugene Boure, Brooklyn, NY (US)

( * ) Notice: Subject to any disclaimer, the term of this patent is extended or adjusted under 35 U.S.C. 154(b) by 792 days.

(21) Appl. No.: 17/390,386

(22) Filed: Jul. 30, 2021

(65) Prior Publication Data
US 2022/0034531 A1    Feb. 3, 2022

Related U.S. Application Data

(60) Provisional application No. 63/170,559, filed on Apr. 4, 2021, provisional application No. 63/059,961, filed on Jul. 31, 2020.

(51) Int. Cl.
| | | |
|---|---|---|
| *F24F 8/22* | (2021.01) | |
| *F24F 13/14* | (2006.01) | |
| *F24F 9/00* | (2006.01) | |

(52) U.S. Cl.
CPC ............ *F24F 8/22* (2021.01); *F24F 13/14* (2013.01); *F24F 2009/007* (2013.01)

(58) Field of Classification Search
None
See application file for complete search history.

(56) References Cited

U.S. PATENT DOCUMENTS

| | | | |
|---|---|---|---|
| 6,855,295 B2 | 2/2005 | Kulp | |
| 7,005,111 B2 | 2/2006 | Bollini | |
| 8,455,843 B1 | 6/2013 | Presser et al. | |
| 9,402,931 B2 | 8/2016 | Engelhard | |
| 10,987,440 B1 | 4/2021 | Sood et al. | |
| 11,060,712 B2 | 7/2021 | Niemiec et al. | |
| 2003/0217641 A1* | 11/2003 | Palestro | A61L 9/20 422/121 |
| 2006/0213157 A1* | 9/2006 | Kalous | F24F 8/158 55/385.2 |
| 2009/0129974 A1 | 5/2009 | McEllen | |
| 2010/0143205 A1* | 6/2010 | Engelhard | A61L 9/20 422/121 |
| 2012/0161039 A1 | 6/2012 | Yoon et al. | |
| 2017/0321877 A1* | 11/2017 | Polidoro | F24F 13/28 |
| 2018/0347574 A1* | 12/2018 | Niemiec | F21S 10/06 |

(Continued)

*Primary Examiner* — Jelitza M Perez
(74) *Attorney, Agent, or Firm* — Alexey Bakman, Esq.

(57) ABSTRACT

Device and method for a UV air sanitizer with boundlessly-extended sanitizing chamber are provided. The device comprises an enclosure with an inlet emitter area with directional louvers. The inlet emitter area optimized for drawing in outside air stream, while simultaneously emitting ultraviolet germicidal radiation into said outside air stream. The device further comprises a fan and a disinfection unit with at least one UV lamp. The UV lamp is uniquely positioned and directed inside the enclosure, so as to simultaneously irradiate: air moving inside the enclosure, air entering through the inlet emitter area, as well as a moving stream of air, said air located outside of the enclosure and drawn toward the inlet area by the fan. The method includes the steps required to use the device for creation of one or multiple germicidally-protective defensive air curtains.

13 Claims, 9 Drawing Sheets

(56) References Cited

U.S. PATENT DOCUMENTS

| | | |
|---|---|---|
| 2018/0368383 A1 | 12/2018 | Ko et al. |
| 2019/0308122 A1* | 10/2019 | Aries .................. F24F 13/06 |
| 2020/0108166 A1 | 4/2020 | Rhoden |
| 2020/0354513 A1 | 11/2020 | Niemiec et al. |

* cited by examiner

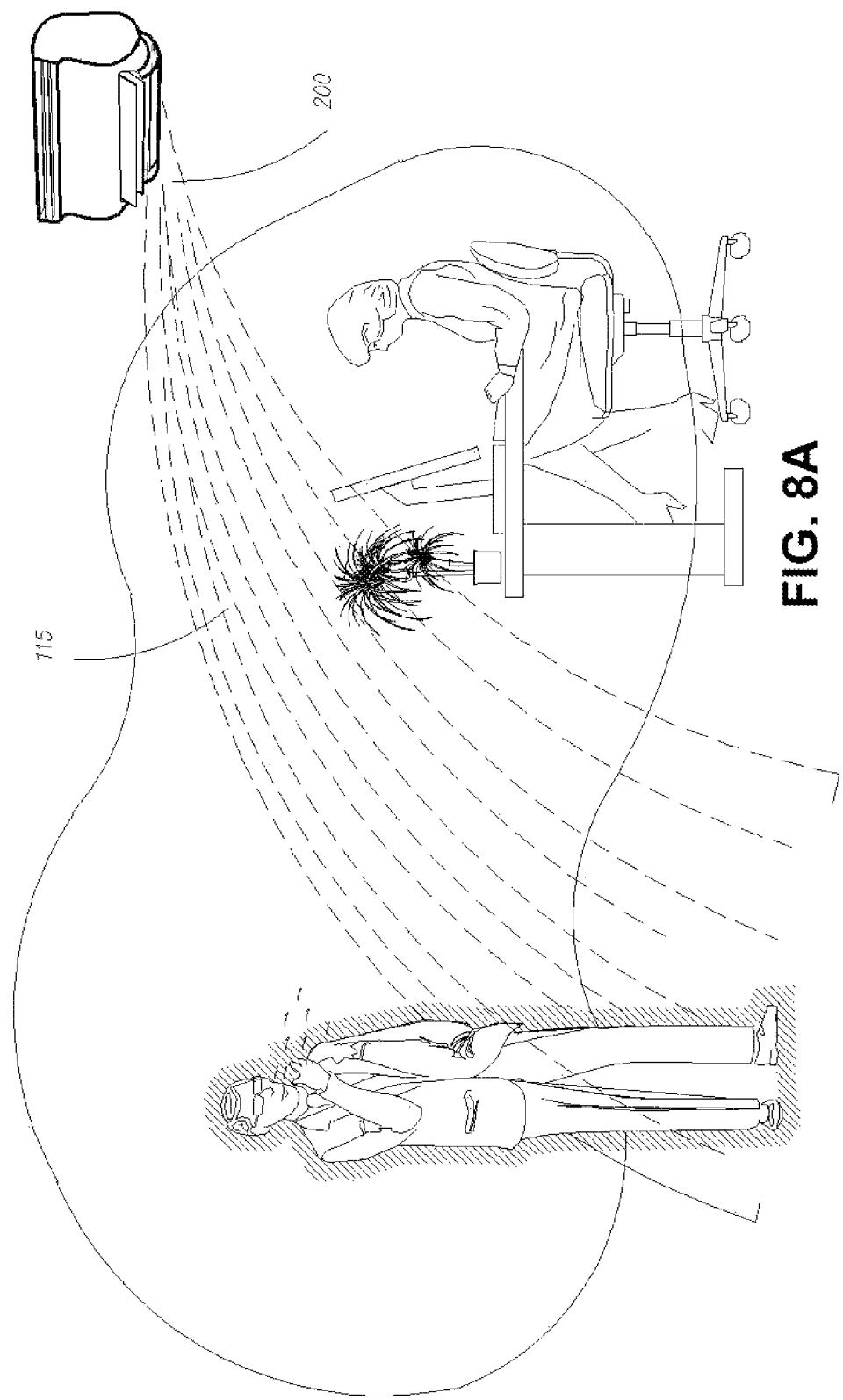

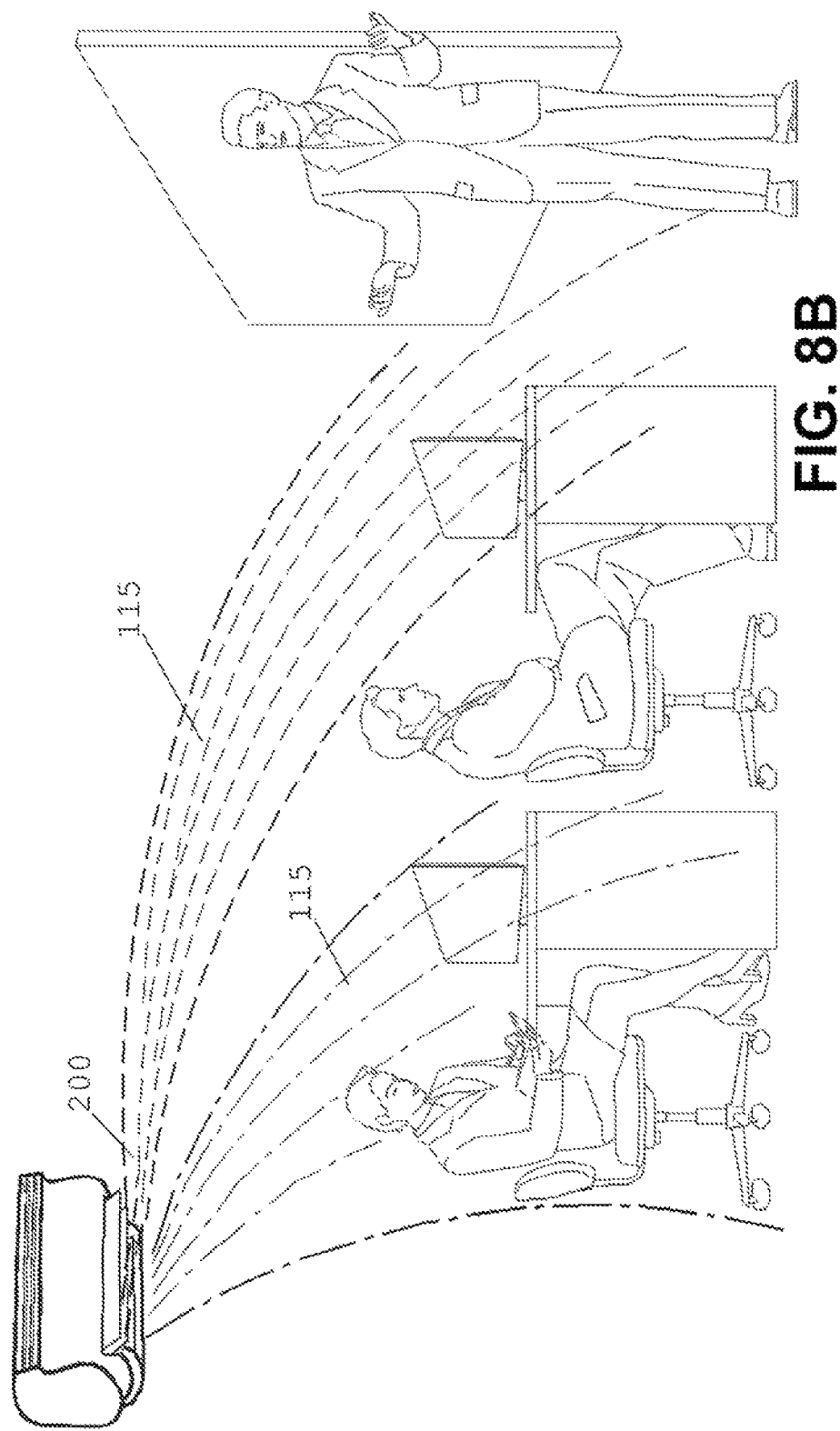

AIR SANITIZER WITH BOUNDLESSLY-EXTENDED SANITIZING CHAMBER AND METHOD OF USING SAME

Present application claims priority to the following previously-filed provisional applications:
- 63/059,961—FORCED CIRCULATION UV AIR DISINFECTOR WITH BOUNDLESS WORKING CHAMBER FOR DISINFECTION AND METHOD OF USING SAME—31 Jul. 2020
- 63/170,559—AIR IRRADIATOR AND RECIRCULATOR WITH BOUNDLESS 360 DEGREE WORKING CHAMBER AND METHOD OF USING SAME—4 Apr. 2021

FIELD OF THE INVENTION

The field of the present invention is Ultraviolet Germicidal Irradiation air purification devices and methods, and particularly, Ultraviolet Germicidal Irradiation air purification devices and methods, utilizing a combination of bounded and boundless working chambers to maximize sanitizing air path, increase sanitizing efficiency, minimize mixing of contaminated and decontaminated air, and to provide defensive sanitized air curtaining within living spaces.

BACKGROUND OF THE INVENTION

Ultraviolet (UV) lamps are well known in the prior art for sanitizing of air and surfaces. Ultraviolet Germicidal Irradiation, emitted by such lamps is highly efficient as part of the strategy to reduce exposure to a number of pathogenic organisms, including viral, bacterial, mycobacterial and fungal organisms. Pathogens, effectively neutralized by this method also include SARS-CoV-2, the virus that causes COVID-19. Ultraviolet Germicidal Irradiation is also effective against prions and multicellular organisms, including multiple species of insects that may be the vectors for infectious diseases.

UV lamps, emitting germicidal irradiation are proved to be highly effective for use in uninhabited spaces, (such as empty laboratories, operating rooms, and hotel rooms). However, use of open UV lamps in inhabited spaces, where humans may be exposed to the radiation, is dangerous due to the possible mutagenic and other effects of UV on human health.

The problems associated with open sanitizing UV light are addressed, in part, by enclosed air sanitizing machines, which can be used in the presence of people. Such air sanitizing machines, utilizing confined UV light, are known in the prior art. Generally, these machines comprise a UV lamp, positioned inside of an enclosed (i.e. bounding) irradiation chamber. The chamber limits the extent of Ultraviolet Germicidal Irradiation to within the bounds of the enclosure, thus preventing escape of the radiation into the surrounding areas. Generally, in these devices, air entering the enclosed bounding chamber is exposed to UV radiation. If the airborne pathogens in the air receive an appropriate amount of UV energy, while passing through the machine, they get killed or inactivated. As the organic contaminants get destroyed, the air is sanitized. This UV-Sanitized air is then expelled into the room.

The obvious advantages of the enclosed air sanitizing machines are that they can be used in the vicinity of people and may utilize a powerful UV light within the bounds of the chamber.

However, this approach also has great deficiencies. While the bounding chamber protects the inhabitants of the dwelling from exposure to direct UV light, it also greatly limits the exposure of air to the UV lamp. Design of a chamber, enclosing a UV sanitizing lamp must necessarily balance conflicting requirements between the size of the chamber and bulkiness of the end-product. A bounding chamber that is too small limits the amount of air that can be contained within such sanitizing device at any one time. Small chamber also limits the amount of time that air may actually be exposed to the effects of UV radiation. An excessively large UV-enclosing bounding chamber would be more efficient, but would necessarily take up more room in the dwelling, interfering with the use of space. A bounding chamber that is so light-proof, as to prevent escape of any UV radiation may also contribute to overheating of the UV lamp, thus not only reducing lamp's useful service life, but also limiting the size and/or power of a lamp that may be used within such an enclosure.

Also known in the art are the air sanitizing fixtures that openly emit ultraviolet germicidal irradiation, but limit such radiation to uninhabited upper portions of the room. Such fixtures are usually attached to the walls or the ceiling of the premises and emit radiation into the space, above the heads of room occupants. This creates a narrow horizontal field of ultraviolet rays in the upper portions of the room. Theoretically, as contaminated air moves throughout the room, some of it rises into the field and gets exposed to the UV rays. If airborne pathogens receive an appropriate amount of UV energy, while positioned in the field, they will be neutralized.

However, this approach also has a number of deficiencies. If there is limited air flow in the room, then air in the top portions of the dwelling will be primarily sanitized, while the air in the lower portions will remain primarily untreated. As occupants of the room are positioned in the lower portions of the room, they are still able to breath in unsanitized air and to transmit pathogens to each other via aerosol by talking, coughing and sneezing.

If, on the other hand, a room has significant airflow (provided by natural air draft, fans or other ventilation systems), then a random flow of air will be moving through the horizontal field of ultraviolet rays. As pathogens briefly pass in and out of the field, suspended in the moving air, most of them are unlikely to be exposed for sufficient amounts of time to be neutralized. But even if the randomly circulating air, briefly exposed to the field, is sufficiently sanitized, such air then travels down and mixes with unsanitized air below. While this approach may reduce the overall concentration of pathogens in the inhabited space, it does not preclude random hotspots of pathogen concentration throughout the space.

For example, we can assume that a particular occupied public room has a device of the type presently known in the art. Such device is emitting ultraviolet germicidal irradiation in a horizontal field, over the heads of inhabitants. The room has some circulation of air, so that the air in the lower portions of the room is gradually mixing with sanitized air in the upper portion of the room. One of the inhabitants of the room is contagiously ill. He or she suddenly sneezes, releasing an aerosol of virus-laden microscopic droplets. Regardless of the UV field above and regardless of the general circulation of air, for at least a brief period of time, a cloud of viral mucous remains suspended around the sneezing individual. If another person is located nearby or walks past, in one breath they may inhale sufficient pathogenic load to become contaminated. Furthermore, as air randomly circulates, pathogens will be spread by moving air throughout the lower portion of the room before some of them get caught in the updraft and get exposed to the UV radiation. Others may mixed in with previously-sanitized air and be carried throughout the room to be inhaled. If pathogens released in a sneeze are virulent enough or released in great quantity, all people located in the room may be sufficiently exposed to become ill before contaminated air eventually becomes mixed and diluted with sanitized air to safe levels. Thus, the present approaches to air sanitization, do not allow for efficient protection of inhabitants against sudden concentrated releases of pathogenic organisms into the air.

In light of the deficiencies found in existing approaches to UV air sanitizing, there is a long-felt and unmet need for a device that would overcome issues inherent in prior art. Such device should occupy minimum dwelling space, while at the same time protecting inhabitants from direct exposure to UV radiation. The device would also expose large quantities of air to the effects of UV radiation, and keep such exposure for extended periods of time to neutralize pathogens. The device must exceed the exposure efficiency achievable by both the bounding chamber devices and the UV field devices of the present art. In other words, such device must be essentially boundless in its air sanitizing functionality, while having all of the advantages of a fully bounded UV box device. The device must not only sanitize the entire volume of air in the room, but must, at the same time prevent significant mixing of unsanitized air into sanitized air streams. It must also be capable of protecting inhabitants against unexpected coughs, sneezes and other sudden concentrated releases of pathogenic organisms into the air.

The device and method of the present invention achieve all of these objectives and provide numerous additional benefits.

SUMMARY OF THE PRESENT INVENTION

The present invention is defined by the following claims and nothing in this section should be taken as a limitation on those claims.

A UV air sanitizing device with boundlessly-extended sanitizing chamber, described and claimed in the present invention comprises the following elements. The device comprises an enclosure. The enclosure has an inlet emitter area, featuring a plurality of inlet directional louvers. The inlet directional louvers are positioned to extend parallel to a ceiling.

The inlet emitter area is optimized for drawing in outside air stream, while simultaneously emitting ultraviolet germicidal radiation into the same outside air stream. A fan is positioned inside the enclosure and is configured for drawing air from outside the enclosure through the inlet emitter area;

The device further comprises an outlet curtaining area, optimized for precisely directing and sustaining a protective curtain of sanitized air. The internal air passage space, inside the enclosure has walls and extends from the inlet emitter area to the outlet curtaining area.

Apparatus of the present invention further features a disinfection unit that comprises at least one UV lamp. The UV lamp is positioned inside the enclosure and is positioned and spatially directed to simultaneously: irradiate air moving inside the enclosure, irradiate air entering and moving through the inlet emitter area, as well as to irradiate a moving stream of outside air, drawn toward the inlet emitter area by the fan.

In the preferred embodiments of the invention, the inlet emitter area is positioned in the top side of the enclosure. In some preferred variants, the outlet curtaining area comprises at least one outlet directional louver, movingly attached to the outlet curtaining area.

The method implements the device of the present invention and comprises the steps of: positioning the device in a habitable space and ensuring that the outlet curtaining area is positioned above the heads of all room inhabitants. Further steps include ensuring that inlet directional louvers are pointed in a direction that is essentially parallel to a ceiling, so as to maximize the reach of ultraviolet germicidal radiation emitted from the inlet emitter area.

Some of the described and claimed steps involve moving the outlet directional louvers, so as to direct the flow of purified air directly at an area, intended for protection from contaminated air, thus creating an area of positive air pressure in the vicinity of the area, intended for protection. Depending on the structure of the device, the present method allows user to direct the plurality of outlet directional louvers, so as to create a plurality of simultaneous independent air streams. The user may then direct the plurality of simultaneous independent air streams of purified air at varying angles, thus creating a plurality of protective air curtains.

BRIEF DESCRIPTION OF THE DRAWINGS

FIG. 8A depicts a preferred embodiment of the present invention in use. The at least one outlet directional louver, is adjusted, so as to precisely direct the flow of purified air to create a protective air curtain in front of an area.

FIG. 8B depicts a preferred embodiment that comprises a plurality of outlet directional louvers, capable of movement independently of each other. The louvers are directed so as to create a plurality of simultaneous independent air streams directed down at varying angles, creating a plurality of protective air curtains.

DETAILED DESCRIPTION OF THE PREFERRED EMBODIMENT

Figure 1:
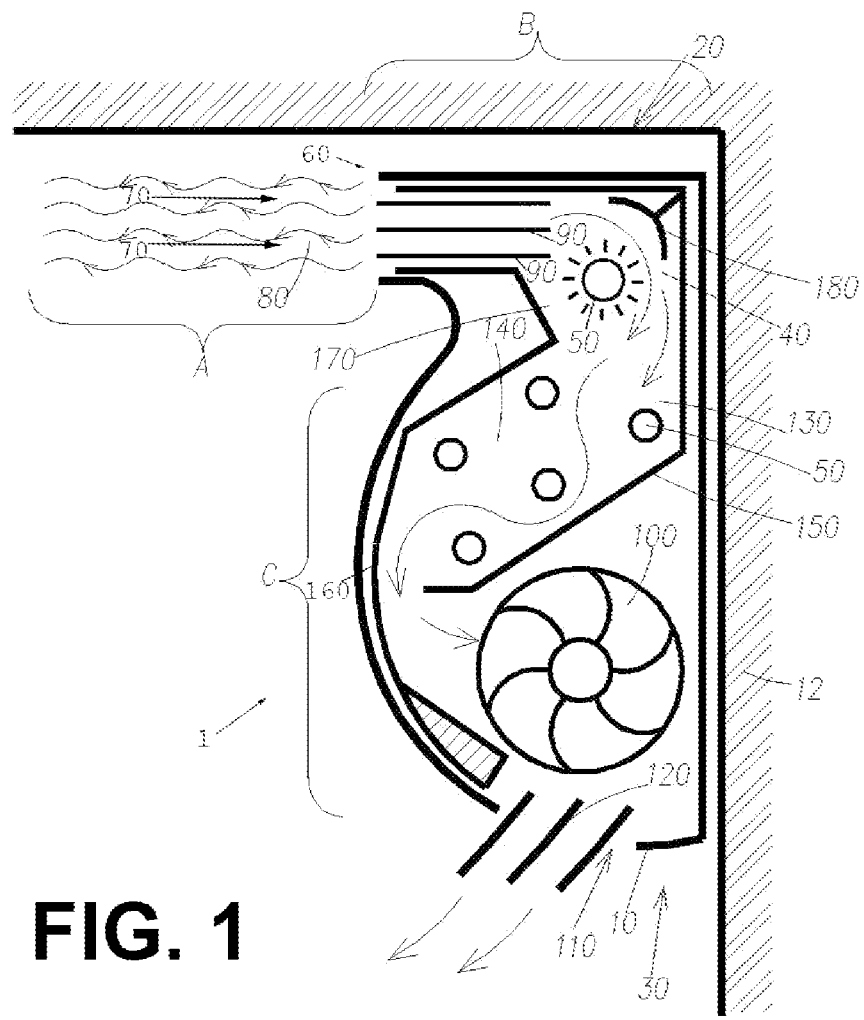
FIG. 1 depicts a schematic view of a preferred embodiment of the device of the present invention, illustrating, among other things, a variant of the device, intended for positioning on a wall.

The device and method of the present invention provide numerous advantages over prior art. One such advantage is that the structure of the present device allows for a greatly increased exposure of air to sanitizing Ultraviolet Germicidal Irradiation, as compared to other UV sanitizing devices, intended for use in the presence of humans. Present invention allows for all of the advantages of machines with enclosed irradiation chambers. Such advantages include using powerful UV emitters within the bounds of the chamber, which shields the occupants of the room. At the same time, the present invention avoids the deficiencies of the machines with enclosed irradiation chambers. In the present invention, the size of the chamber/enclosure does not limit the amount of air that gets exposed at any given time, nor does the size of the chamber limit the exposure time.

In the present invention, the exposure of air to Ultraviolet Germicidal Irradiation begins long before the air enters the chamber/enclosure. Preferred embodiments are configured to produce a stream of air that is drawn in a straight line towards the device, in the upper portions of the room. As the airstream flows towards the device, it is exposed to UV rays that emanate from the device. The UV rays are aimed into and through the stream of incoming air, extending horizontally along the ceiling, over the heads of occupants. The rays, emanating from the device essentially extend the functionality of the bounded portion of the irradiation chamber to the length of the room, thus creating air sanitizer with an essentially "boundless chamber". This creates air sanitizing path (A+B+C, shown on drawings) that is considerably longer than that of the traditional "bounded" sanitizers of prior art and exposes air to higher doses and longer exposure times than traditional irradiating fixtures that can be used in occupied spaces. In essence, the present invention sanitizes air in several distinct stages, ensuring the highest safety of air processed through the device.

In contrast to sanitizers of the prior art, that either rely on local air intake (enclosed chamber devices) or random air movement in an out of the UV field (germicidal field-emitting devices) device and method of the present invention create a directed moving stream of air. Same air caught in the air stream, created by the present invention, passes though all the stages of purification. This prevents the problem, found in UV-field emitters of the prior art, where randomly-moving air is exposed to various intensities of irradiation for varying periods of time and then mixed in with untreated air. Prior art approach creates patches of untreated or insufficiently-treated air in the room and allows for concentrations of pathogens. While enclosed-chamber devices of the prior art may sanitize most of the air they draw in, such air is typically drawn in and expelled in direct vicinity of the device, This allows for sanitizing of nearby sections of the room, creating highly localized zones, where purified air mixes with contaminated air, creating dangerous zones of deceptive safety. The device and method of the present invention allow for immediate purification of air both, within the enclosure and throughout the length of the "boundless chamber", which is only limited by the size of the room. Directed moving stream of air, created by the device of the present invention allows for immediate purification of air throughout the room as soon as the device and method of the present invention are activated.

The device and method of the present invention further utilize the assuredly-purified air that passes through all the purification stages to create air curtains and defined safety zones throughout the living space, as described below.

The device and method of the present invention will now be illustrated by reference to the accompanying drawings. Preferred embodiments of the Air Sanitizer With Boundlessly-Extended Sanitizing Chamber and Method of Using Same have been assigned reference numeral 1. Other elements have been assigned the reference numerals referred to below.

Figure 2:
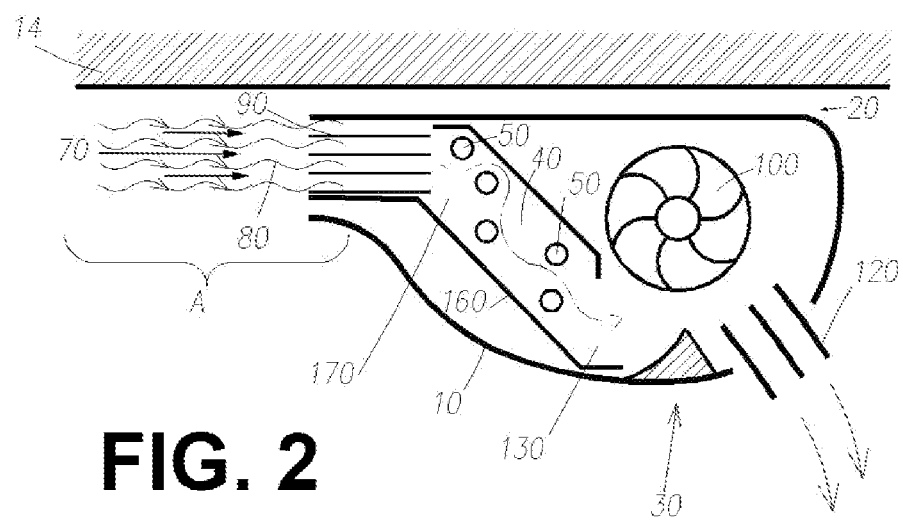
FIG. 2 depicts a schematic view of one of the preferred embodiments of the device of the present invention, illustrating, among other things, a variant of the device, intended for positioning on a ceiling.
Figure 3:
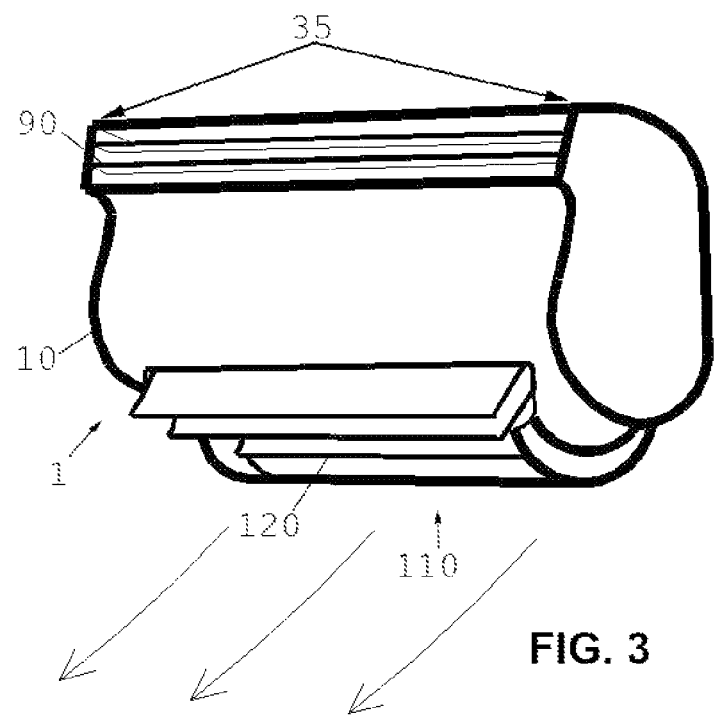
FIG. 3 depicts a perspective side view of one of the preferred embodiments of the device of the present invention, of the wall-mounted type.
Figure 4:
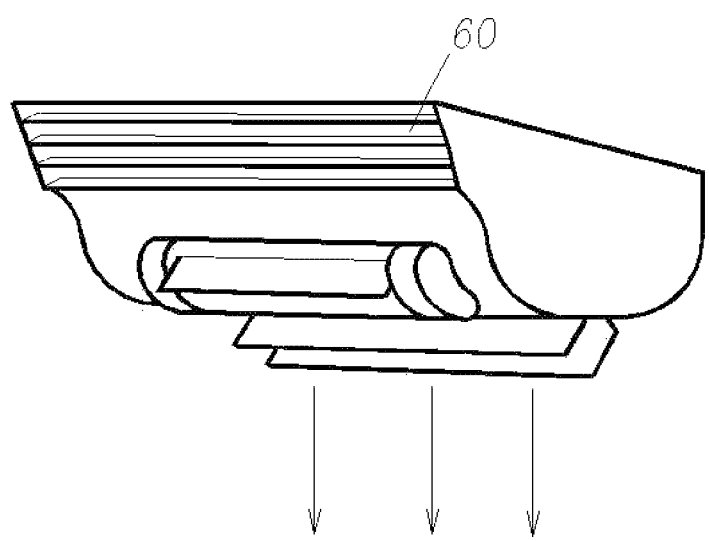
FIG. 4 depicts a perspective side view of one of the preferred embodiments of the device of the present invention, of the ceiling-mounted type.

Air sanitizer and method comprise an enclosure 10. In the preferred variants, the enclosure 10 is made of plastic, although in other variants, it may be made out of thin metal, wood or other materials. In preferred embodiments, the enclosure 10 is vertically-elongated shape and intended for mounting on a wall 12, in the upper part of the living space, as illustrated in FIG. 1 and FIG. 3. However, it is foreseeable that enclosure 10 may be of the type, mountable on the ceiling 14, as illustrated in FIG. 2 and FIG. 4. Alternatively, the enclosure 10 may be of the floor-standing type (FIG. 5) or have other installation options, as may be evident to one skilled in the art.

The enclosure 10 comprises a top side 20, a bottom side 30, and a width 35. It further comprises a disinfection unit 40, positioned inside the enclosure 10. The disinfection unit 40 comprises at least one UV lamp 50 (UV lamp 50). The UV lamp 50 is adapted to emit light in the UVC band of UV light. That is, the band with germicidally-effective wavelength, ranging between 200-280 nm. In preferred embodiments, the wavelength, emitted by the at least one UV lamp 50 approaches 265 nm, which is the peak wavelength for germicidal activity.

It should be noted that the term "UV lamp" is a general term that refers to wide range of artificial sources of germicidal (or insecticidal) UV irradiation. Such sources of UV light may include, but are not limited to LED UV lights, high and low pressure mercury lamps, excimer lamps and other sources of germicidal UV irradiation, known to those skilled in the art. It is foreseeable that in some embodiments of the invention a plurality of UV sources (such as several identical UV lamps) may be used. It is also foreseeable that UV light sources of different physical nature and intensity may be combined in a single device. For example it is possible that in some variants, one type of UV light source may be used to treat air inside the enclosure 10, while another type of UV light source may be used to direct light outside the enclosure 10.

One preferred embodiment of the invention utilizes UV-emitting LED with the power of 30 Watts. However, the preferred number and intensity of functional LED lamps in each particular device will vary, but may be easily determined by those skilled in the art. The results of the determination will depend on the size of the device, on size and crowdedness of the room to be disinfected, the speed of air flow toward and through the device, and on the type and UV-resistance of pathogen to be neutralized, among other factors. For example, if the device and the room are large, the space is crowded, and the organisms to be neutralized include tough gram-positive spore-forming bacteria, then accordingly more powerful sources of UV irradiation must be used than would be required in other circumstances.

The enclosure 10 further comprises an inlet emitter area 60. The inlet emitter area 60 is so-named due to the fact that this same area is optimized for and serves as an inlet for drawing in a moving stream of air 70 from outside the enclosure 10. Simultaneously it also serves as an emitter of a field of ultraviolet germicidal radiation 80 that emanates from the device 1 into the moving stream of air 70 (outside air stream 70).

The inlet emitter area 60 comprises a plurality of inlet directional louvers 90 (inlet louvers 90). In preferred variants, inlet louvers 90 are positioned horizontally. They extend along the width 35 of the enclosure 10, so as to draw in the inbound stream of air 70 horizontally, parallel to the ceiling, and to direct emanating rays of ultraviolet germicidal radiation 80 on the same horizontal path, in direction away from the enclosure 10, directly opposite to the inbound stream of air 70. It is foreseeable that in some embodiments inlet louvers 90 are slanted in a position other than horizontal. A non-horizontal positioning of the inlet louvers 90 may be relevant in situations where the ceiling of the room has a slant and it is preferable to direct the inbound stream of air 70 and the emanating rays of ultraviolet germicidal radiation 80 parallel to the ceiling.

Figure 9:
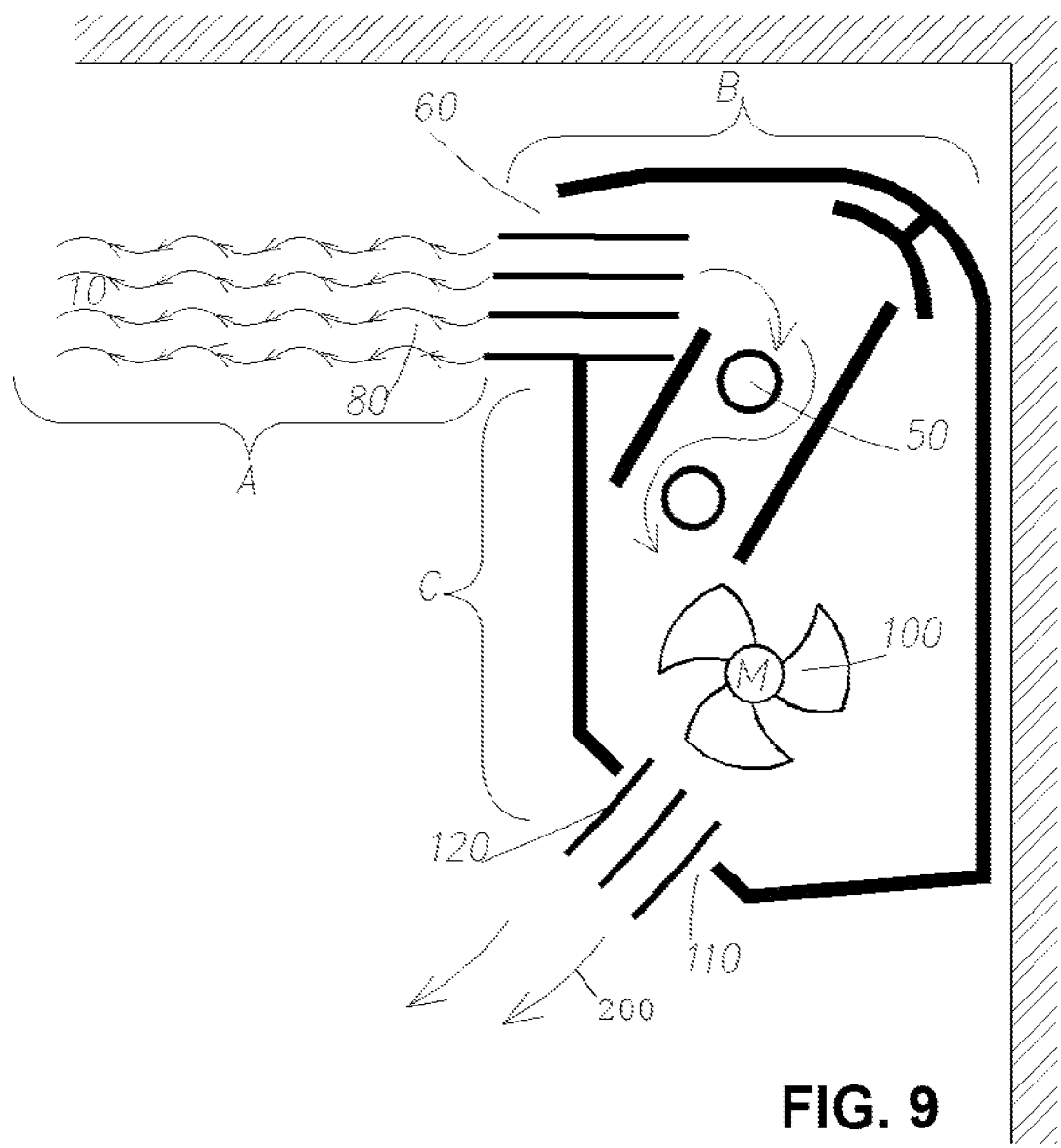
FIG. 9 illustrates one of the preferred embodiments of the device of the present invention, positioned on a wall. The depiction shows, among other things, the "boundless" nature of the device, wherein the rays of sanitizing ultraviolet light effect air not only within the bounds of the device (section B and C), but also extend potentially "boundlessly," limited only by walls of a room, and sanitizing air beyond the bounds of the device (section A).
Figure 10:
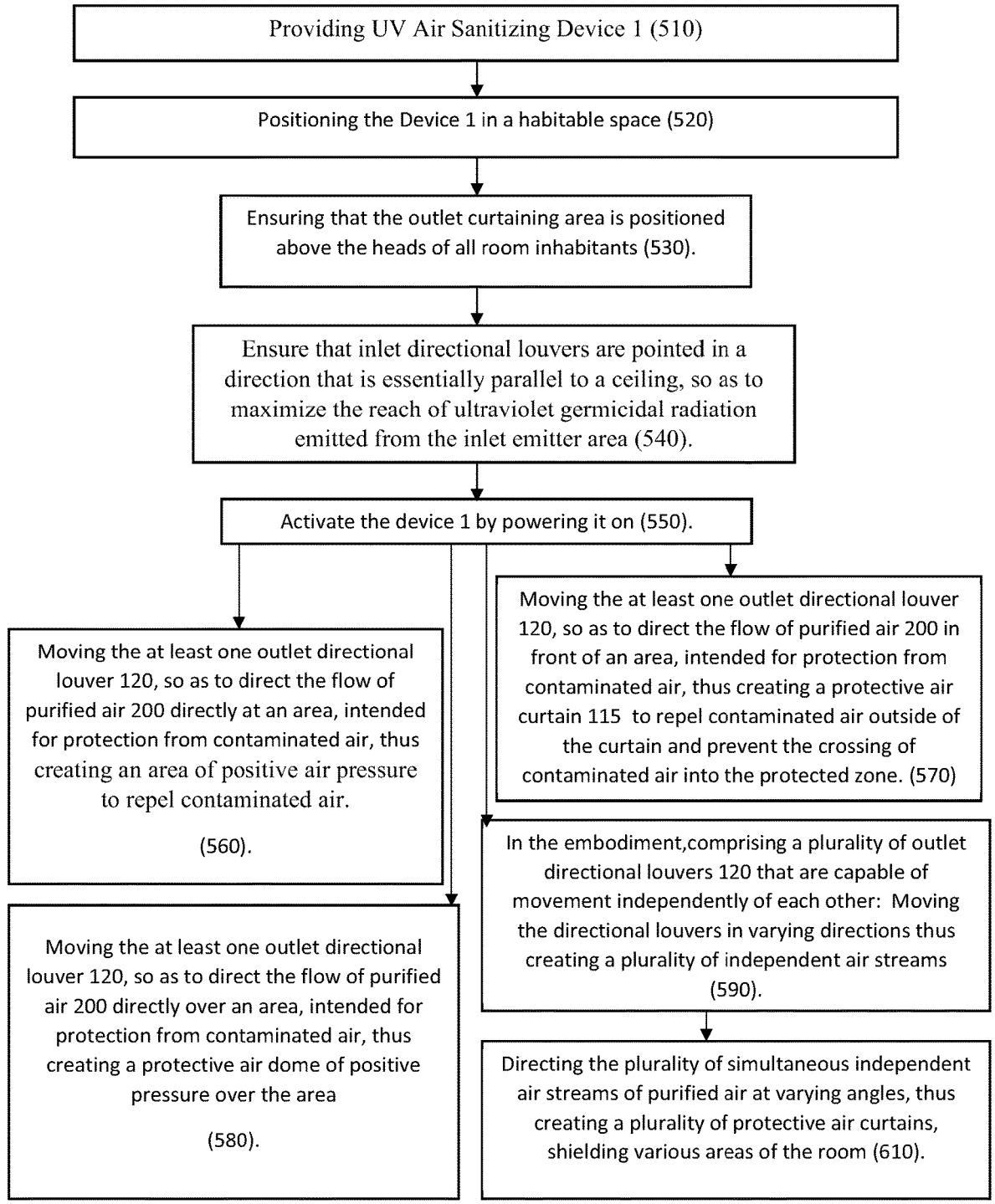
FIG. 10 is a flow chart, illustrating the method of the present invention.

The enclosure 10 comprises at least one fan 100, positioned within the enclosure. The fan 100 is configured for drawing in air stream from outside the enclosure through an inlet emitter area 60. The term "fan" is a broad term that refers to any adaptation for drawing in air through the inlet louvers 90. In the preferred embodiments, the fan 100 is a traditional bladed fan, as illustrated on FIG. 9. In other variants of the invention, other methods of air transport (such as Air Multiplier™ technology (Registered Trademark of Dyslon Limited) or ionic technology) may be used.

The enclosure 10 further comprises an outlet curtaining area 110. The outlet curtaining area 110 is optimized for precisely directing and sustaining a curtain of sanitized air. That is, the outlet curtaining area 110 allows user to precisely direct a stream (or streams) of sanitized air in order to create invisible protective air curtains 115, as illustrated in FIG. 8. As present invention allows for longer air exposure to germicidal UV rays than prior art purifiers, and as design of the present invention prevents mixing of treated and untreated air, air emanating from the outlet curtaining area 110 is highly sanitized. This air can be safely used to create one or more areas of positive pressure throughout the room that would be impervious to pathogens, traveling through the air. Positive pressure, created in such areas would repel contaminated air and any suddenly-released pathogenic aerosols (such as from a sneeze) from the protected area.

Figure 7:
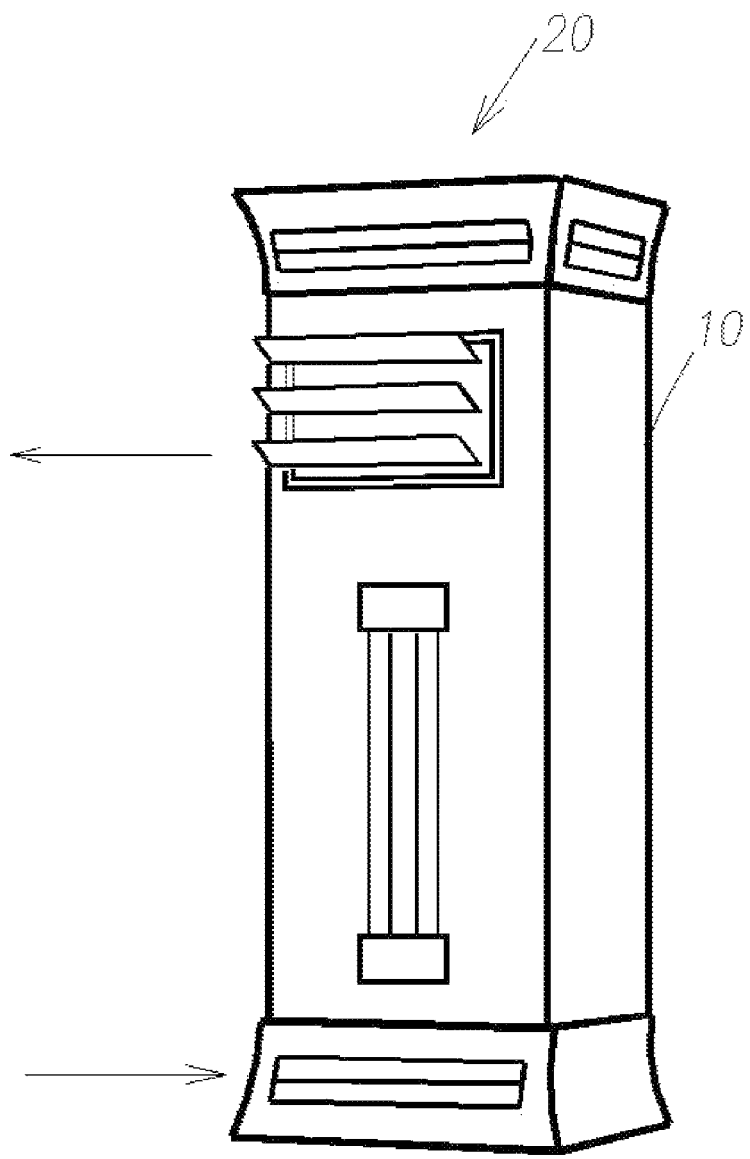
FIG. 7 depicts a perspective side view of one of the preferred embodiments of the device of the present invention, of the floor-standing type.

In order to effectuate room curtaining and to create safe zones, the outlet curtaining area 110 comprises at least one outlet directional louver 120 (outlet louver 120) (FIG. 1, FIG. 7). Preferably the outlet curtaining area 110 comprises a plurality of outlet louvers 120. The outlet louvers 120 are preferably movingly attached to the outlet area, allowing the user to precisely direct a curtain 115 (or multiple curtains 115) of treated air over or into the protected area. In the preferred embodiments the outlet louvers are made of plastic, but may be made of metal, wood or a variety of suitable materials, known to those skilled in the art. In some variants of the invention, outlet louvers extend outward beyond outer surface of the enclosure 10, allowing for precise adjustment of the angle of the protective curtain 115.

The enclosure 10 also comprises an internal air passage space 130. The internal air passage space 130 has an internal length 140. The internal length 140 essentially extends from the inlet emitter area 60 to the outlet curtaining area 110 and defines the length of the "bounded chamber" 150 of the device 1. The internal length 140 comprises walls of the passage space 160 (internal walls 160).

In preferred devices and methods of this invention, the at least one UV lamp 50 is positioned inside the enclosure 10. This UV lamp 50 is positioned and spatially directed/oriented in an unusual, non-traditional way. In bounded/enclosed irradiators of the prior art, UV lamps are positioned in a way, so as to be fully shielded by the enclosure, preventing UV light from escaping into the room. In the present invention, the at least one UV lamp 50 is positioned and oriented in such a way, as to simultaneously, irradiate air moving through the internal air passage space 130 inside the enclosure 10, while simultaneously irradiating air entering and moving through the inlet emitter area 60. At the same time the at least one UV lamp 50 is positioned and angled so as to irradiate a moving stream of air 70, said stream located outside of the enclosure 10 and drawn toward the inlet area by the fan 100. In preferred embodiments of the invention, the at least one UV lamp 50 is positioned inside the inlet emitter area 60, inside the enclosure 10. Such positioning allows some of the germicidal light to shine through the inlet louvers 90, thus creating the field of ultraviolet germicidal radiation 80.

This field of ultraviolet germicidal radiation 80 in essence extends the sanitizing functionality of the device 1 and the overall length and time of the sanitizing function far beyond the internal air passage space 130 and its internal length 140. The field of ultraviolet germicidal radiation 80 extends out of the device 1 as far as the size of the room allows. Theoretically, only the wall, opposite to the device 1 limits the extent of the field of germicidal radiation 80. This field 80 creates the "boundlessly-extended sanitizing chamber" for the device of the present invention. The field is "boundless" because only the structure of the room limits the reach of its rays. In a way, the entire room becomes an extension of the sanitizing chamber.

As the device of the present invention is turned on, the field of germicidal radiation 80 extends along the ceiling the entire length of the room. As the fan 100 draws the inbound stream of air 70 towards the device of the present invention, the streamlined air is continually exposed to the sanitizing effects of the UV light emanating from the inlet louvers 90 for as long as it travels the distance to the inlet louvers 90 (such distance is indicated as distance "A" on FIG. 1). As the air enters into the device 1 through the louvers 90 and continues to travel horizontally into the machine, it is still continuously exposed to the light emitted by the at least one UV light 50. This portion of the sanitizing path is indicated with a letter "B" on FIG. 1. As the air descends through the internal passage space 130, it continues to be sanitized by the at least one UV lamp 50. This portion of the sanitizing path is indicated with a letter "C" on FIG. 1. Combined, the sanitizing paths A, B and C provide for the longest sanitizing path of any UV air sanitizer.

In preferred embodiments, such as the ones shown on FIG. 1 and FIG. 7, an inlet emitter area 60 is positioned in the top side 20 of the enclosure 10. The enclosure 10 further comprises a curve area 170. The curve area 170 is preferably also positioned in the top side 20, inside the case 10, behind the inlet emitter area 60. This is the location where the air flowing horizontally through inlet emitter area 60 makes a vertical (preferably downward turn) as it continues to travel through the bounded chamber 150. Preferred embodiments of FIGS. 1 and 7, illustrate positioning at least one UV lamp 50 in the curve area 170, so that its rays simultaneously treat air in the outside moving stream of air 70, in the internal air passage space 130, as well as air entering and moving through the inlet emitter area 60 and the curve area 170.

In order to improve efficiency of germicidal irradiation and in order to allow irradiation of germicidal rays from multiple angles, some of the preferred embodiments of the invention comprise at least one UV reflector 180 (reflector 180). Said reflector comprises UV-reflective materials. "Reflector" is a general term and refers to any UV-reflective surfaces inside the device 1. The reflectors may be made of reflective aluminum (aluminum reflects 80-90% UV light), or surfaces coated with reflective paints, such as those sold under the trademark LUMACEPT, or a number of other UV-reflective materials, known to those skilled in the art. In some embodiments of the invention, the entire surface of the internal walls 160 may be coated in reflective materials.

Some of the preferred variants comprise at least one reflector 180, positioned inside the internal air passage space 130, adjacently to the inlet emitter area 60, horizontally opposite to the inlet louvers 90. In such embodiments (such as illustrated in the embodiment of FIG. 1), The at least one UV reflector 180 is positioned, so as to be exposed to light, emitted by at least one of the at least one UV lamp 50. The same UV reflector is simultaneously positioned/oriented to reflect and direct the light that it receives from the UV light 50, reflecting/directing the light through the inlet directional louvers 90 into the outside air stream 70.

In embodiments, utilizing reflectors 180, the at least one UV lamp 50 need not be positioned in direct open view of the inlet emitter area 60 in order to radiate its light through the louvers 90. Instead, one or more reflectors 180, positioned in the emitter area 60 may be used to reflect the light of the UV lamp 50, which may be positioned deep within the internal air passage space 130. Thus, in these embodiments, even a single lamp 50 may be positioned and oriented deep within the bowels of the device, and still be capable, (through the use of reflectors 180), of simultaneously irradiating the air in the outside moving stream of air 70, in the internal air passage space 130, as well as air entering and moving through the inlet emitter area 60 and the curve area 170.

In some embodiments of the invention, the internal air passage space 130 comprises a plurality of perpendicular dividers 180 (dividers 180). These dividers are attached to the walls 160 of the passage space, said dividers 180 extending from the walls of the passage space at least partially into the internal air passage space 130 in a direction mostly perpendicular to the flow of air. The dividers extend the time and distance traveled by air through the internal air passage space 130, maximizing air's exposure to germicidal treatments inside the device 1.

In some of the variants, the at least one UV lamp 50 comprises a plurality of UV lamps, as shown in FIG. 1. Such UV lamps 50 are preferably positioned along the length 140 of the internal passage space 130. In variants, that comprise perpendicular dividers 180, the lamps 50 may be positioned adjacently to the dividers 180, so that as the air is exposed to irradiation from a nearby UV lamp, as it slows down, diverts and swirls, passing around the dividers 180.

Figure 5:
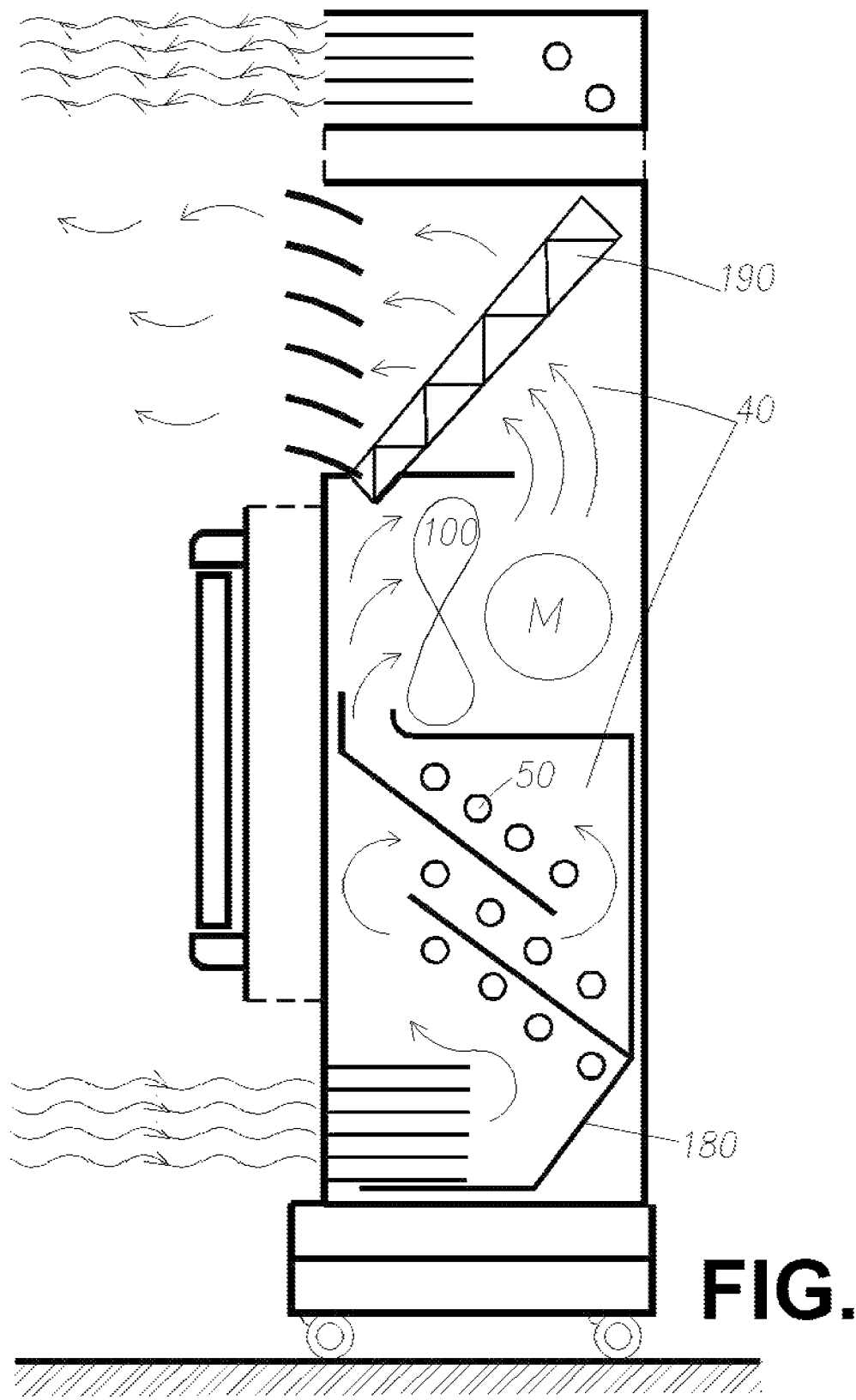
FIG. 5 depicts a schematic cross-sectional view of one of the embodiments of the device of the present invention, wherein the device is of the type adapted for positioning standing the floor.
Figure 6:
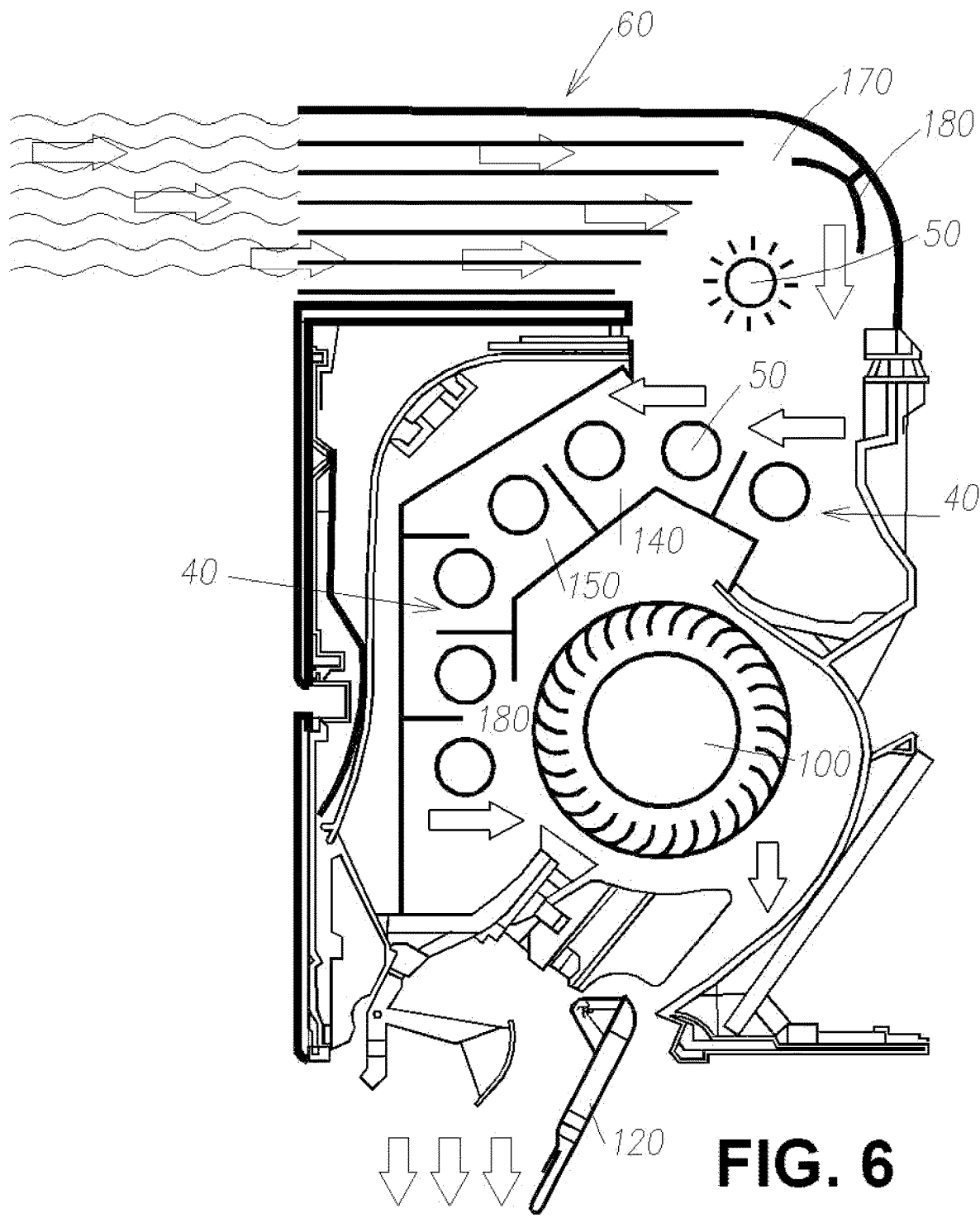
FIG. 6 depicts cross-sectional view of one of the preferred embodiments of the device of the present invention, featuring, among other things, perpendicular dividers and a UV reflector.

The device and method of the present invention do not limit sanitizing treatment of air solely to the exposure to Ultraviolet Germicidal Irradiation. It is foreseeable that some forms of the invention will comprise mechanical particulate air filtration systems, such as HEPA (or finer) filters to trap microscopic particles from the air. It is also foreseeable that some forms will have charcoal filters or chemical filters for absorption of odors or neutralization of harmful chemical compounds. It is also foreseeable that some embodiments will employ chemical compounds on surfaces to catalyze sanitizing effects of Ultraviolet Germicidal Irradiation. The device of FIG. 5 illustrates an embodiment of the invention, comprising a filter 190.

As stated above, in some preferred embodiments of the present device and method, at least one outlet directional louver 120 is a plurality of outlet directional louvers. In some of such embodiments, at least one of the plurality of outlet directional louvers 120 is capable of movement independently of the other outlet directional louvers 120. In other words, in such an embodiment, some of the outlet directional louvers 120 may be pointed to direct air into the room at one angle, while other louvers 120, may direct air into the room at another angle. For example, some of the outlet directional louvers 120 may direct a portion of the sanitized air stream at 210 degree angle away from the device 1, while other outlet directional louvers 120 are directing a portion of the sanitized air at a 240 degree angle, thus creating a plurality of independent air streams. Such air streams may be independently directed to create sanitized air curtains, dividing the room into one or more pathogen-shielded areas.

An example of such use may be in a medical office, where a device of the present invention is positioned on a wall. A field of sanitizing rays extends along the ceiling. A moving stream of air 70 is drawn through the sanitizing field and into the enclosure, where it is further sanitized. The air that was triple-cleaned along the sanitizing paths A+B+C is expelled through the outlet directional louvers 120. The independently-adjustable directional louvers 120 are then directed, so that one curtain of air passes right in front of a receptionist's table under the device 1. The stream of directed air 200 creates an air curtain 115 of positive pressure above and in front of the receptionist. The air curtain 115 ensures that any coughs, sneezes, or airborne air contaminants are repelled away from the receptionist by the positive pressure.

Embodiments that allow for more than one independently-directed stream of air, may allow for a second air curtain 115 to be directed behind the receptionist, thus protecting them from several sides. This may be particularly useful where the person or space to be shielded is located in the middle of a space, such as in the center of a large office. Embodiments that allow for more than one independently-directed stream of air may also be used to create concentrated "air wedges". Streams of air emanating from air purifiers naturally expand, slow down and diverge as they travel away from the purifier. By directing two streams of air at a slight angle toward each other, the streams converge some distance away from the device 1 and reinforce each other, creating effective protective air curtains 115 of positive pressure at significant distances from device 1.

Alternatively, in some embodiments that comprise a plurality of outlet directional louvers 120, user may elect to direct air through only some of the outlet directional louvers 120. Or user may elect to use one stream of air, rather than multiple streams, in order to concentrate emitted air stream, making it as powerful as possible. This would allow for creation of longer-reaching shielding single curtain with high repellency. In such embodiments, at least some of the plurality of outlet directional lovers 120 comprise shutter mechanisms. Such shutter mechanisms shut off the air flow through at least some of the plurality of outlet directional lovers 120, making for more concentrated, more powerful, air flow through the outlet directional lovers 120 that remain open.

Such shutter mechanisms be in the form of vertical sliders directly in front of or directly behind at least some of the outlet directional lovers 120. Movement of the shutters would close or open the flow through some of the directional louvers 120, thus allowing for a more concentrated air stream coming out of open louvers 120. Such stream would travel further and be easier to aim for creation of an air curtain.

It should be noted that while the preferred embodiments of the invention draw in and irradiate a moving stream of air 70 in top portions of the room, along the ceiling, it is foreseeable that some embodiments may also have a capability of irradiating and moving a stream of air 70 in lower portions of the rooms, along the floor. One such floor-standing embodiment is illustrated in FIG. 5. Such embodiments may be useful, among other situations for sanitizing surface of the floor, spaces under furniture or for preventing contamination, found on the floor, from rising into upper levels of the room. This may be particularly useful in such locations as hospitals, medical/microbiological laboratories and clean rooms, where floors may be contaminated by the occupants, but upper surfaces must remain sterile. In preferred variants of such embodiments a moving stream of air is drawn at very low altitudes, along the floor or as close as possible to the floor (mere inch or less off the floor). Likewise the field of ultraviolet germicidal radiation 80, emanating in the direction opposite to the field of ultraviolet germicidal radiation 80, extends out of the device 1 in direct contact with or in very close vicinity to the floor.

It is foreseeable that some embodiments of the invention, especially floor-standing models may be reversible. That is, such variants of the invention may be used as described above (by drawing and sanitizing air along the ceiling), while the room is occupied. The same embodiments may be activated in reverse, when the room is unoccupied, so that the stream of air 70 is drawn and sanitized along the floor. In such embodiments, the functionality of outlet directional louvers 120 and inlet louvers 90 may be reversed when functionality is reversed. Such embodiments comprise additional UV lamps 50 or reflectors 180 in the bottom side of the device 1, so as to allow the emanation of the field of germicidal radiation 80 from the outlet directional louvers 120.

The method for using the device of the present invention comprises the step of providing a UV air sanitizing device 1 of the type described above, and comprising the elements described above (510). The device is then preferably positioned in a habitable space (520), ensuring that the outlet curtaining area is positioned above the heads of all room inhabitants (530).

Another step requires the user to ensure that inlet directional louvers are pointed in a direction that is essentially parallel to a ceiling, so as to maximize the reach of ultraviolet germicidal radiation emitted from the inlet emitter area (540). The user then activates the device 1 by powering it on (550).

The method further comprises an optional step of moving the at least one outlet directional louver 120, so as to direct the flow of purified air 200 directly at an area, intended for protection from contaminated air (560). This step creates an area of positive air pressure in the vicinity of the area, intended for protection. As the area of positive air pressure is created by sanitized air from the device 1, contaminated air is repelled from the area.

Another optional step involves moving the at least one outlet directional louver 120, so as to direct the flow of purified air 200 in front of an area, intended for protection from contaminated air. (570). The user, thus creates a protective air curtain 115. This curtain of positive air pressure repels contaminated air outside of the curtain, preventing the crossing of contaminated air into the protected zone.

The method comprises another optional step of moving the at least one outlet directional louver 120, so as to direct the flow of purified air 200 directly over an area, intended for protection from contaminated air, thus creating a protective air dome over the area (580).

In yet another step of the method, the at least one outlet directional louver 120 comprises a plurality of outlet directional louvers 120. These outlet directional louvers 120 are capable of movement independently of each other. The movement of directional louvers in varying directions thus creates a plurality of independent air streams (590). In this step, the user directs the plurality of outlet directional louvers 120, so as to split the stream of air 200 into a plurality of simultaneous independent air streams (600).

The user then directs the plurality of simultaneous independent air streams of purified air at varying angles, thus creating a plurality of protective air curtains, shielding various areas of the room (610).

It is to be understood that while the apparatus and method of this invention have been described and illustrated in detail, the above-described embodiments are simply illustrative of the principles of the invention and the forms that the invention can take, and not a definition of the invention. It is to be understood also that various other modifications and changes may be devised by those skilled in the art, which will embody the principles of the invention and fall within the spirit and scope thereof. It is not desired to limit the invention to the exact construction and operation shown and described. The spirit and scope of this invention are limited only by the spirit and scope of the following claims.

We claim:
1. A UV air sanitizing device, comprising:
  a. an enclosure, said enclosure comprising:
    i. a top side,
    ii. a bottom side,
    iii. a width,
    iv. an inlet emitter area, said inlet emitter area comprising:
      1. a plurality of inlet directional louvers, said inlet directional louvers positioned externally, said inlet directional louvers positioned to extend parallel to a ceiling along the width of the enclosure,
      2. said inlet emitter area optimized for drawing in outside air stream, while simultaneously emitting ultraviolet germicidal radiation into said outside air stream;
    v. an outlet curtaining area,
      1. Said outlet curtaining area optimized for precisely directing and sustaining a curtain of sanitized air;
    vi. an internal air passage space,
      1. Said internal air passage space having an internal length, extending from the inlet emitter area to the outlet curtaining area, and
      2. comprising walls of the passage space;
    vii. a disinfection unit, said disinfection unit comprising at least one UV lamp;
    viii. at least one fan, said fan configured for drawing air from outside the enclosure through the inlet emitter area; and b. wherein at least one of the at least one UV lamp is positioned inside the enclosure, said at least one of the at least one UV lamp positioned and spatially directed to simultaneously:
   i. irradiate air moving inside the enclosure,
   ii. irradiate air entering and moving through the inlet emitter area,
   iii. as well as to irradiate a moving stream of air, said stream located outside of the enclosure and drawn toward the inlet emitter area by the fan,
c. wherein the at least one UV lamp is adapted to emit light in the UVC band of UV light,
d. wherein
   i. the inlet emitter area, said inlet emitter area configured for emitting ultraviolet germicidal radiation outside of the enclosure onto a moving stream of air is positioned in the top side of the enclosure; and
   ii. the outlet curtaining area is positioned on the bottom side of the enclosure and comprises at least one outlet directional louver, said at least one outlet directional louver movingly attached to the outlet curtaining area.

2. The device of claim 1, further comprising at least one UV reflector, said at least one UV reflector
   i. comprising UV-reflective materials;
   ii. wherein said at least one UV reflector is positioned inside the internal air passage space, adjacently to the inlet emitter area, wherein
   iii. said at least one UV reflector positioned, in a location of exposure to light, emitted by at least one of the at least one UV lamp,
   iv. said at least one UV reflector positioned and oriented to reflect and direct the light, emitted by at least one of the at least one UV lamp, through the inlet directional louvers in the inlet emitter area into the outside air stream.

3. The device of claim 1, wherein the enclosure comprises a curve area, said curve area
   positioned in the top side of the enclosure, and behind the inlet emitter area, and wherein
   at least one of the at least one UV lamp is positioned inside the curve area, the at least one UV lamp positioned and spatially directed to allow at least some of the UV light to emit through the inlet emitter area.

4. The device of claim 3, wherein:
   the internal air passage space comprises a plurality of perpendicular dividers, wherein said dividers are
   a. attached to the walls of the passage space,
   b. said dividers extending from the walls of the passage space partially into the internal air passage space, so as to extend distance traveled by air through the internal air passage space.

5. The device of claim 4, wherein the at least one UV lamp comprises a plurality of UV lamps, said plurality of UV lamps positioned along the length of the internal air passage space.

6. The device of claim 5, wherein the at least one outlet directional louver comprises a plurality of outlet directional louvers, and wherein at least one of the plurality of outlet directional louvers is capable of movement independently of the other outlet directional louvers, thus creating a plurality of independent air streams.

7. The device of claim 1, wherein the internal air passage comprises a mechanical particulate air filtration filter.

8. The device of claim 1, wherein the at least one UV lamp comprises a plurality of internally-positioned UV lamps, and wherein at least one of the plurality of internally-positioned UV lamps is positioned and spatially directed to simultaneously:
   a. irradiate air entering and moving through the outlet curtaining area,
   b. as well as to irradiate a moving stream of air, said stream located outside of the enclosure and drawn toward the outlet curtaining area by the fan.

9. A method for air sanitizing, comprising the steps of:
a. providing a UV air sanitizing device of the type comprising:
   i. an enclosure, said enclosure comprising:
      1. a top side,
      2. a bottom side,
      3. a width,
   ii. an inlet emitter area, configured for emitting ultraviolet germicidal radiation, said inlet emitter area comprising:
      1. a plurality of inlet directional louvers, said inlet directional louvers positioned externally, said inlet directional louvers positioned to extend parallel to a ceiling along the width of the enclosure,
      2. said inlet emitter area configured for drawing in outside air stream, while simultaneously emitting ultraviolet germicidal radiation from inside the enclosure into said outside air stream;
   iii. an outlet curtaining area,
      1. said outlet curtaining area optimized for precisely directing and sustaining a curtain of sanitized air;
   iv. an internal air passage space,
      1. said internal air passage space having an internal length, extending from the inlet emitter area to the outlet curtaining area, and
      2. comprising walls of the passage space;
   v. a disinfection unit, said disinfection unit comprising at least one UV lamp;
   vi. at least one fan, said fan configured for drawing air from outside the enclosure through the inlet emitter area;
b. wherein at least one of the at least one UV lamp is positioned inside the enclosure, said at least one of the at least one UV lamp positioned and spatially directed to simultaneously:
   i. irradiate air moving inside the enclosure,
   ii. irradiate air entering and moving through the inlet emitter area,
   iii. as well as to irradiate a moving stream of air, said stream located outside of the enclosure and drawn toward the inlet emitter area by the fan,
c. wherein the at least one UV lamp is adapted to emit light in the UVC band of UV light,
d. wherein
   i. the inlet emitter area, said inlet emitter area configured for emitting ultraviolet germicidal radiation outside of the enclosure onto a moving stream of air is positioned in the top side of the enclosure;
   ii. the outlet curtaining area is positioned on the bottom side of the enclosure and comprises at least one outlet directional louver, said at least one outlet directional louver movingly attached to the outlet curtaining area,
e. positioning the device in a habitable space,
f. ensuring that the outlet curtaining area is positioned above the heads of all room inhabitants;
g. ensuring that inlet directional louvers are pointed in a direction that is essentially parallel to a ceiling, so as to maximize the reach of ultraviolet germicidal radiation emitted from the inlet emitter area;

h. activating the device by powering it on.

10. The method of claim 9, further comprising the step of moving the at least one outlet directional louver, so as to direct the flow of purified air directly at an area, intended for protection from contaminated air, thus creating an area of positive air pressure in the vicinity of the area, intended for protection.

11. The method of claim 10, further comprising the step of moving the at least one outlet directional louver, so as to direct the flow of purified air in front of an area, intended for protection from contaminated air, thus creating a protective air curtain in front of the area.

12. The method of claim 9, further comprising the step of moving the at least one outlet directional louver, so as to direct the flow of purified air directly over an area, intended for protection from contaminated air, thus creating a protective air dome over the area.

13. The method of claim 9, wherein the at least one outlet directional louver comprises a plurality of outlet directional louvers, and wherein at least one of the plurality of outlet directional louvers is capable of movement independently of the other outlet directional louvers, thus creating a plurality of independent air streams;

further comprising the step of directing the plurality of outlet directional louvers, so as to create a plurality of simultaneous independent air streams, and further directing the plurality of simultaneous independent air streams of purified air at varying angles, thus creating a plurality of protective air curtains.

* * * * *